United States Patent
Fujimori

(10) Patent No.: US 12,015,045 B2
(45) Date of Patent: Jun. 18, 2024

(54) MANUFACTURING METHOD OF IMAGE PICKUP APPARATUS FOR ENDOSCOPE, IMAGE PICKUP APPARATUS FOR ENDOSCOPE, AND ENDOSCOPE

(71) Applicant: OLYMPUS CORPORATION, Tokyo (JP)

(72) Inventor: Noriyuki Fujimori, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 450 days.

(21) Appl. No.: 17/375,532

(22) Filed: Jul. 14, 2021

(65) Prior Publication Data

US 2021/0343779 A1    Nov. 4, 2021

Related U.S. Application Data

(63) Continuation of application No. PCT/JP2019/001883, filed on Jan. 22, 2019.

(51) Int. Cl.
| | |
|---|---|
| *H01L 27/146* | (2006.01) |
| *H04N 23/55* | (2023.01) |
| *H04N 23/50* | (2023.01) |

(52) U.S. Cl.
CPC ............ *H01L 27/14685* (2013.01); *H01L 27/14618* (2013.01); *H01L 27/14625* (2013.01);
(Continued)

(58) Field of Classification Search
CPC ......... H01L 27/14685; H01L 27/14618; H01L 27/14625; H01L 27/14687; H04N 23/55;
(Continued)

(56) References Cited

U.S. PATENT DOCUMENTS

| | | |
|---|---|---|
| 2013/0162882 A1 | 6/2013 | Rudmann et al. |
| 2018/0246258 A1* | 8/2018 | Shiraiwa ............ G02B 13/0085 |

(Continued)

FOREIGN PATENT DOCUMENTS

| | | |
|---|---|---|
| EP | 3369363 A1 | 9/2018 |
| JP | 2006-292927 A | 10/2006 |

(Continued)

OTHER PUBLICATIONS

International Search Report dated Apr. 9, 2019 issued in PCT/JP2019/001883.

*Primary Examiner* — Mohammad M Hoque
(74) *Attorney, Agent, or Firm* — Scully, Scott, Murphy & Presser, P.C.

(57) ABSTRACT

A manufacturing method of an image pickup apparatus for endoscope includes: manufacturing two optical wafers each of which has a glass wafer as a base substrate and is a hybrid lens wafer including a plurality of resin lenses, and a spacer wafer including a plurality of spacers and being formed with an inorganic material; manufacturing a bonded wafer in which space in which the plurality of resin lenses are disposed is hermetically sealed by directly bonding the two optical wafers and the spacer wafer at a temperature lower than a softening point of the plurality of resin lenses; disposing a plurality of image pickup members on the bonded wafer; and cutting the bonded wafer on which the plurality of image pickup members are disposed.

5 Claims, 8 Drawing Sheets

(52) U.S. Cl.
CPC ....... *H01L 27/14687* (2013.01); *H04N 23/55* (2023.01); *H04N 23/555* (2023.01)

(58) Field of Classification Search
CPC ..... H04N 23/555; A61B 1/0011; A61B 1/051; G02B 13/0085; G02B 23/243; G02B 23/24
USPC ......................................................... 257/432
See application file for complete search history.

(56) References Cited

U.S. PATENT DOCUMENTS

| | | | |
|---|---|---|---|
| 2018/0303325 A1 | 10/2018 | Fujimori | |
| 2018/0324336 A1 | 11/2018 | Wan et al. | |
| 2019/0079280 A1* | 3/2019 | Yoshida | ............ H01L 27/14618 |
| 2020/0054201 A1* | 2/2020 | Fujimori | ................ A61B 1/051 |

FOREIGN PATENT DOCUMENTS

| | | | |
|---|---|---|---|
| JP | 2008-283002 A | | 11/2008 |
| JP | 2010-056292 A | | 3/2010 |
| JP | 2011-107588 A | | 6/2011 |
| JP | 2012-018993 A | | 1/2012 |
| JP | 2013-531812 A | | 8/2013 |
| JP | 2013531812 A | * | 8/2013 |
| JP | 2015-038538 A | | 2/2015 |
| JP | 2017-032799 A | | 2/2017 |
| JP | 2017-047169 A | | 3/2017 |
| JP | 2018-042935 A | | 3/2018 |
| WO | 2011/156926 A1 | | 12/2011 |
| WO | 2017/022193 A1 | | 2/2017 |
| WO | 2017/072847 A1 | | 5/2017 |
| WO | 2017/073440 A1 | | 5/2017 |
| WO | 2017/203592 A1 | | 11/2017 |
| WO | 2017/203593 A1 | | 11/2017 |
| WO | 2018/198266 A1 | | 11/2018 |

* cited by examiner

MANUFACTURING METHOD OF IMAGE PICKUP APPARATUS FOR ENDOSCOPE, IMAGE PICKUP APPARATUS FOR ENDOSCOPE, AND ENDOSCOPE

CROSS REFERENCE TO RELATED APPLICATION

This application is a continuation application of PCT/JP2019/001883 filed on Jan. 22, 2019, entire contents of which are incorporated herein by this reference.

BACKGROUND OF THE INVENTION

1. Field of the Invention

The present invention relates to a manufacturing method of an image pickup apparatus for endoscope including an optical member including a resin lens, the image pickup apparatus for endoscope including the optical member including the resin lens, and the endoscope including the image pickup apparatus for endoscope including the optical member including the resin lens.

2. Description of the Related Art

Making an image pickup apparatus for endoscope smaller is important to achieve a less-invasive endoscope.

Examples of a method for efficiently manufacturing a small image pickup apparatus can include a wafer level manufacturing method in which a bonded wafer obtained by bonding a plurality of device wafers each including a plurality of optical devices is cut.

Japanese Patent Application Laid-Open Publication No. 2012-18993 discloses an image pickup module including a wafer level stacked body. The image pickup module is manufactured by bonding an optical wafer including a plurality of optical devices and an image pickup wafer including a plurality of image pickup devices and cutting and separating the bonded wafer into pieces.

Japanese Patent Application Laid-Open Publication No. 2015-38538 discloses a so-called hybrid lens device in which a lens formed with a resin is disposed on a parallel flat glass plate.

By manufacturing an optical member including a plurality of hybrid lens devices using a wafer level method, it is possible to efficiently manufacture a small-diameter image pickup apparatus having a small external size in an optical axis orthogonal direction.

SUMMARY OF THE INVENTION

A manufacturing method of an image pickup apparatus for endoscope of an embodiment of the present invention includes manufacturing two optical wafers each having a glass wafer as a base substrate, at least one of the two optical wafers being a hybrid lens wafer including a plurality of resin lenses, and a spacer wafer which includes a plurality of spacers and which is formed with an inorganic material, manufacturing a bonded wafer in which space in which the plurality of resin lenses are respectively disposed is hermetically sealed, and which includes the two optical wafers and the spacer wafer by directly bonding the spacer wafer to the two optical wafers at a temperature lower than a softening point of the plurality of resin lenses in a state where the spacer wafer is put between the two optical wafers, disposing a plurality of image pickup members on the bonded wafer, and manufacturing the image pickup apparatus for endoscope including an optical member which includes two optical devices each having a glass plate as a base substrate and a spacer which is disposed between the two optical devices, and each of the plurality of image pickup members by cutting the bonded wafer in which the image pickup member in plurality are disposed.

An image pickup apparatus for endoscope of another embodiment of the present invention includes an optical member which includes two optical devices each having a glass plate as a base substrate, and a spacer which is disposed between the two optical devices and which is formed with an inorganic material, at least one of the two optical devices being a hybrid lens device including a resin lens, and an image pickup member configured to receive light of an object image, the light being focused by the optical member, and space in which the resin lens is disposed is hermetically sealed by the optical device being directly bonded to the spacer.

An endoscope of another embodiment of the present invention includes an image pickup apparatus for endoscope, the image pickup apparatus for endoscope including an optical member which includes two optical devices each having a glass plate as a base substrate and a spacer which is disposed between the two optical devices and which is formed with an inorganic material, at least one of the two optical devices being a hybrid lens device including a resin lens, and an image pickup member configured to receive light of an object image, the light being focused by the optical member, and space in which the resin lens is disposed is hermetically sealed by the optical devices being directly bonded to the spacer.

DETAILED DESCRIPTION OF THE PREFERRED EMBODIMENTS

<Endoscope>

Figure 1:
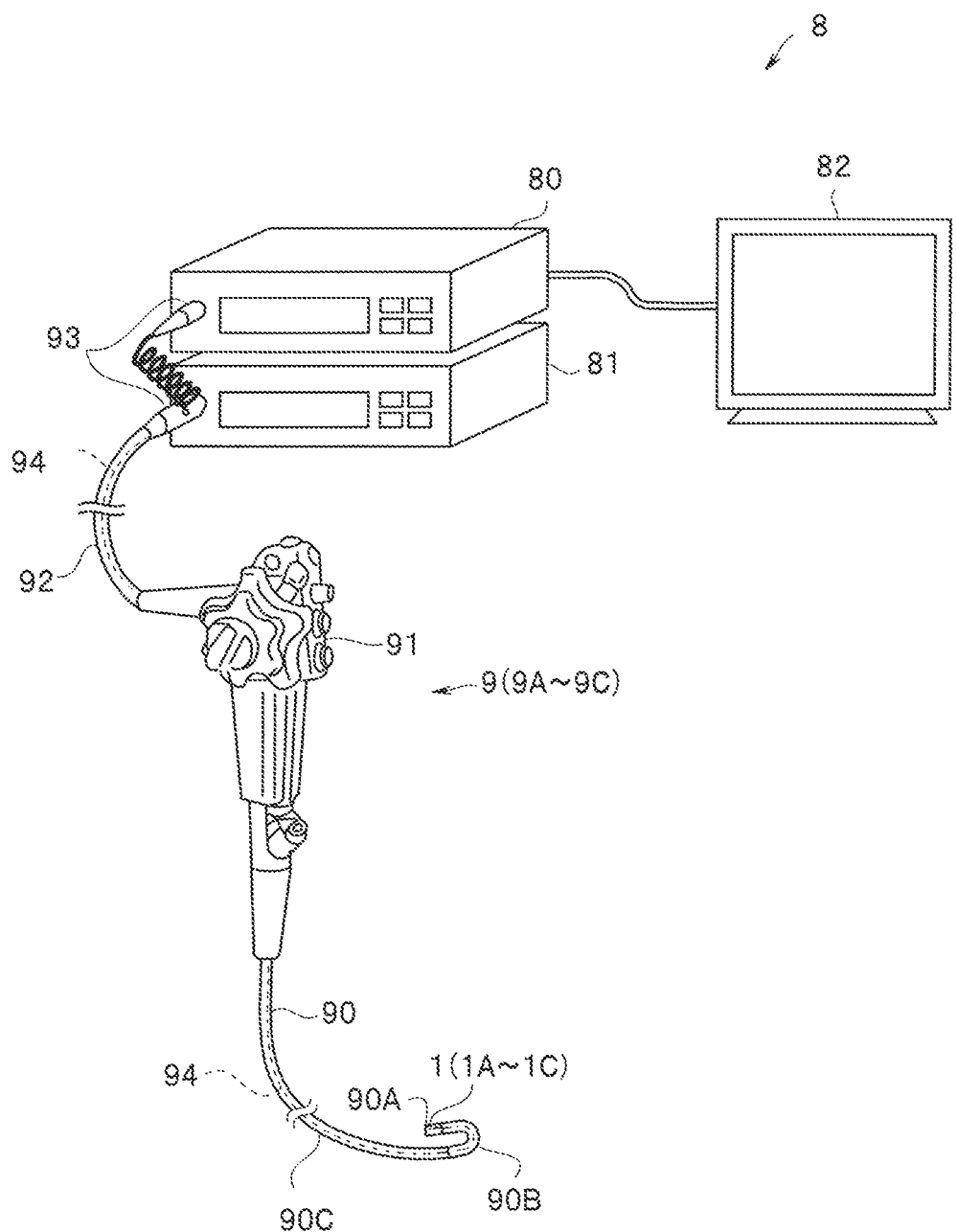
FIG. 1 is a perspective view of an endoscope system including an endoscope of embodiments.

As illustrated in FIG. 1, an endoscope system 8 including an endoscope 9 of an embodiment includes a processor 80, a light source apparatus 81, and a monitor 82. The endoscope 9 photographs inside of a body of a subject by an insertion portion 90 being inserted into a body cavity of the subject, and outputs an image pickup signal.

An operation portion 91 at which various kinds of buttons for operating the endoscope 9 are provided is disposed at a proximal end portion of the insertion portion 90 of the endoscope 9. The insertion portion 90 includes a rigid distal end portion 90A at which an image pickup apparatus for endoscope 1 is disposed, a bending portion 90B which is connected to the proximal end portion of the rigid distal end portion 90A and which can freely bend, and a flexible portion 90C connected to a proximal end portion of the bending portion 90B. The bending portion 90B bends through operation at the operation portion 91.

A universal cord 92 extending from the operation portion 91 is connected to the processor 80 and the light source apparatus 81 by way of a connector 93. The insertion portion 90, the operation portion 91 and the universal cord 92 allow insertion of a signal cable 94 which transmits an electrical signal outputted from the image pickup apparatus for endoscope 1.

The processor 80 controls the whole of the endoscope system 8, performs signal processing on an image pickup signal outputted from the image pickup apparatus for endoscope 1, and outputs the image pickup signal subjected to the signal processing as an image signal. The monitor 82 displays the image signal outputted from the processor 80.

The light source apparatus 81 includes, for example, a white LED. Illumination light emitted from the light source apparatus 81 is guided to the rigid distal end portion 90A by way of a light guide (not illustrated) which passes through the universal cord 92 and the insertion portion 90 and illuminates an object.

The image pickup apparatus for endoscope 1 of the endoscope 9 has a small diameter as will be described later, and has excellent resistance to moisture, and thus, the endoscope 9 is less invasive and has excellent resistance to moisture.

Note that while the endoscope 9 is a medical flexible endoscope, an endoscope of another embodiment may be an industrial endoscope or a rigid endoscope.

First Embodiment

Figure 2:
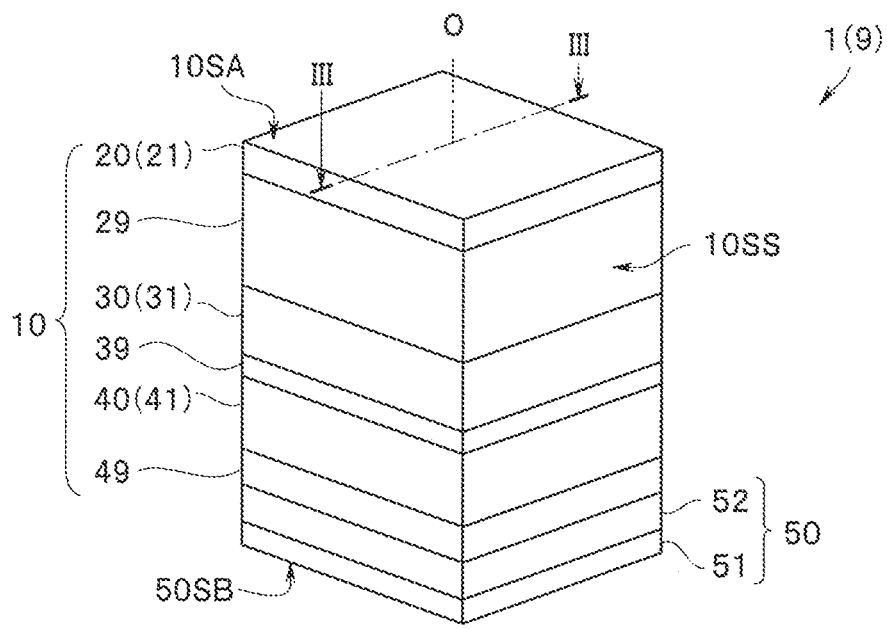
FIG. 2 is a perspective view of an image pickup apparatus for endoscope of a first embodiment.
Figure 3:
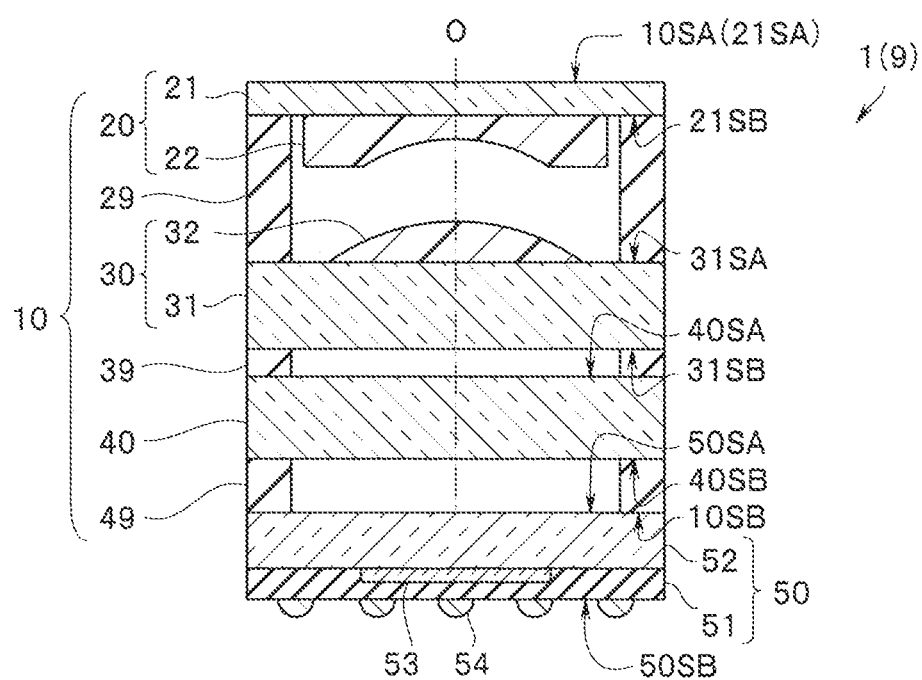
FIG. 3 is a cross-sectional diagram of the image pickup apparatus for endoscope of the first embodiment, cut along a line in FIG. 2.

As illustrated in FIG. 2 and FIG. 3, the image pickup apparatus for endoscope 1 (hereinafter, also referred to as an "image pickup apparatus 1") of the present embodiment includes an optical member 10 and an image pickup member 50.

In the following description, the drawings based on the respective embodiments schematically illustrate the image pickup apparatus. Relationship between a thickness and a width of each portion, a ratio of thicknesses of respective portions, or the like, are different from actual relationship, ratio, or the like. Part of relationship of dimensions and ratios are different between the drawings. Illustration of part of components and assignment of reference numerals will be omitted. A direction of an object will be referred to a "front" direction.

The optical member 10 is a quadrangular prism having an entrance surface 10SA, a rear surface 10SB facing the entrance surface 10SA, and four side surfaces 10SS. The optical member 10 is a wafer level stacked body in which a plurality of optical devices 20, 30 and 40 and a plurality of spacers 29, 39 and 49 are bonded. The spacers 29, 39 and 49 respectively have through-holes which become optical path regions. As will be described later, the optical member 10 is manufactured by cutting a bonded wafer 10W obtained by bonding a plurality of optical wafers 20W, 30W and 40W and a plurality of spacer wafers 29W, 39W and 49W (see FIG. 5), and thus, a plurality of optical devices 20, or the like, have the same external size in a direction orthogonal to an optical axis O, and the four side surfaces 10SS are cut surfaces.

The optical devices 20 and 30 are hybrid lens devices which have glass plates 21 and 31 as base substrates and in which resin lenses 22 and 32 are disposed. The resin lenses 22 and 32 are formed with a transparent resin for lens, for example, an acrylic resin or an epoxy resin.

The image pickup member 50 includes a front surface 50SA and a back surface 50SB facing the front surface 50SA. The image pickup member 50 includes an image pickup device 51 and a cover glass 52. The front surface 50SA of the cover glass 52 is bonded to the rear surface 10SB of the optical member 10. An object image, light of which is focused by the optical member 10 is converted into an electrical signal by a light receiving region 53 of the image pickup device 51, and the electrical signal is outputted from an external electrode 54 on the back surface 50SB.

Intervals between the optical devices 20 and 30, between optical devices 30 and 40 and between the optical device 40 and the image pickup member 50 are respectively defined by the spacers 29, 39 and 49. The spacers 29, 39 and 49 are formed with silicon which has low moisture permeability and which is an inorganic material, and a region constituting an optical path is a cylindrical space.

Note that as will be described later, materials of the spacers 29, 39 and 49 may be ceramics such as glass and silicon nitride, or a metal such as gold, titanium and aluminum if the materials are inorganic materials which can be respectively directly bonded to the optical devices 20, 30 and 40 and the cover glass 52 and which have low moisture permeability. Further, types of glass of the glass plates 21 and 31, the optical device 40 and the cover glass 52 are not limited to borosilicate glass or silica glass and may be, for example, sapphire glass if the glass is a transparent inorganic material which can be directly bonded to the spacers 29, 39 and 49 and which has low moisture permeability.

The optical device 20 is a hybrid lens device including a glass plate 21 having a first principal surface 21SA and a second principal surface 21SB facing the first principal surface 21SA, and an aspheric concave lens 22 which is disposed on the second principal surface 21SB and which is formed with a resin. The first principal surface 21SA is the entrance surface 10SA of the optical member 10. The optical device 30 is a hybrid lens device including a glass plate 31 having a third principal surface 31SA and a fourth principal surface 31SB facing the third principal surface 31SA, and an aspheric convex lens 32 which is disposed on the third principal surface 31SA and which is formed with a resin.

The optical device 40 having a fifth principal surface 40SA and a sixth principal surface 40SB facing the fifth principal surface 40SA is an infrared cut filter device which has a function of blocking infrared light and which is formed with glass, and does not include a resin lens. In other words, the optical member 10 only requires to include optical devices, at least one of which is a hybrid lens device.

Note that a configuration of the optical member 10, that is, a type, the number and stacking order of the optical devices can be variously modified in accordance with specifications. For example, a patterned light shielding film having an aperture function may be disposed on a principal surface of the optical device.

In other words, the optical member 10 includes at least two optical devices and a spacer disposed between the two optical devices. However, the optical member of the embodiment of the present invention only requires to include at least two optical devices respectively having glass plates as base substrates, and one spacer which is disposed between the two optical devices and which is formed with an inorganic material, at least one of the two optical devices being a hybrid lens device including a resin lens.

Note that a resin lens is not disposed on the first principal surface 21SA of the optical device 20 which is a first optical device disposed at a fore most part closest to the object among the plurality of optical devices 20, 30 and 40, that is, on the entrance surface 10SA of the optical member 10.

The side surface 10SS of the optical member 10 is not exposed outside in a case where the image pickup apparatus 1 is stored in the rigid distal end portion 90A of the endoscope 9. However, the entrance surface 10SA of the optical member 10 (the first principal surface 21SA of the optical device 20) is exposed. In other words, the image pickup apparatus 1 is disposed at the endoscope 9 in a state where the optical device on the most distal end side of the image pickup apparatus 1 is exposed from a distal end surface of the endoscope 9. Reliability of the resin lens is not sufficient compared to reliability of a glass lens. Further, there is a possibility that the exposed resin lens may be broken.

The image pickup apparatus 1, in which a resin lens is not disposed on the entrance surface 10SA of the optical device 20, has high reliability.

Further, as will be described later, portions to be bonded of the plurality of optical devices 20, 30 and 40 are respectively directly bonded to portions to be bonded of the plurality of spacers 29, 39 and 49. Here, direct bonding refers to a form in which atoms exposed on respective bonding surfaces bind to each other on a bonding interface of two members to be bonded without use of a bonding member such as an adhesive.

As a method for direct bonding, for example, an SAB (surface-activated bonding) or Anodic Bonding is used as will be described later.

Note that other members such as an adhesive are not put between the bonding surfaces of the two members which are directly bonded. In other words, two members between which other members are not put can be regarded as being directly bonded.

The image pickup apparatus 1 includes the optical member 10 constituted with a wafer level stacked body, and thus, has a small diameter. Further, the resin lenses 22 and 32 can be easily manufactured and are inexpensive. While the resin lenses 22 and 32 have high moisture absorbency, space in which the resin lenses 22 and 32 are disposed is surrounded by the glass plates 21 and 31 which are directly bonded to the spacer 29 formed with silicon and hermetically sealed, and thus, the image pickup apparatus 1 excels in resistance to moisture. The endoscope 9 including the image pickup apparatus 1 is less invasive and excels in resistance to moisture.

It is necessary to dispose a moisture-resistant film on the side surfaces to secure moisture resistance in the image pickup apparatus in which the optical devices of the optical member are bonded to the spacers with an adhesive. The image pickup apparatus 1 of the present embodiment has high resistance to moisture, which eliminates necessity of disposing a moisture-resistant film or which only requires a thin moisture-resistant film, so that a small-diameter image pickup apparatus 1 can be achieved.

Note that a thermal expansion coefficient $\alpha 29$ of the spacer 29 is preferably equal to or greater than 50% and equal to or less than 200% of thermal expansion coefficients $\alpha 21$ and $\alpha 31$ of the glass plates 21 and 31. The thermal expansion coefficient $\alpha$ within such a range makes thermal stress applied on the bonding surface small even if a temperature changes upon bonding or when used, so that high reliability of the image pickup apparatus 1 can be achieved.

For example, the thermal expansion coefficient $\alpha 29$ of the spacer 29 formed with silicon is 3.9 ppm/° C. In this case, glass of a type which makes the thermal expansion coefficients $\alpha 21$ and $\alpha 31$ equal to or greater than 1.95 ppm/° C. and equal to or less than 7.8 ppm/° C., for example, borosilicate glass is preferably selected as the glass plates 21 and 31.

<Manufacturing Method of Image Pickup Apparatus>

Figure 4:
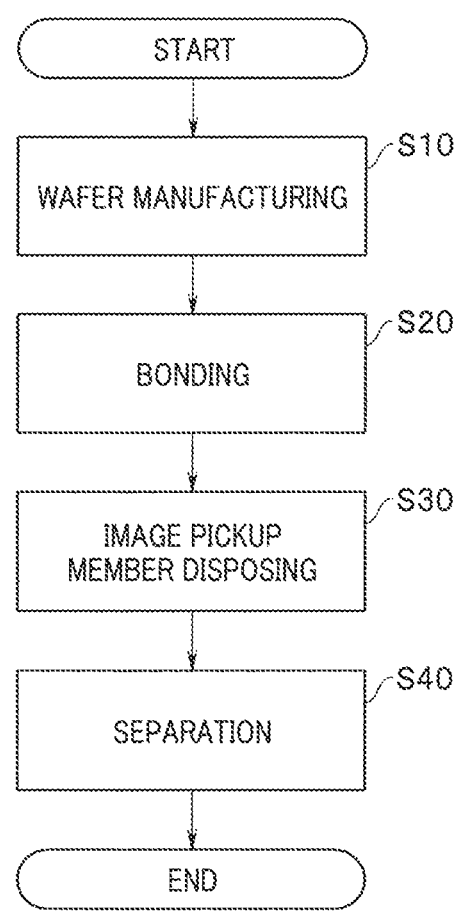
FIG. 4 is a flowchart of a manufacturing method of the image pickup apparatus for endoscope of the first embodiment.

A manufacturing method of the image pickup apparatus for endoscope 1 will be described next along a flowchart illustrated in FIG. 4.

<Step S10> Wafer Manufacturing Process

Figure 5:
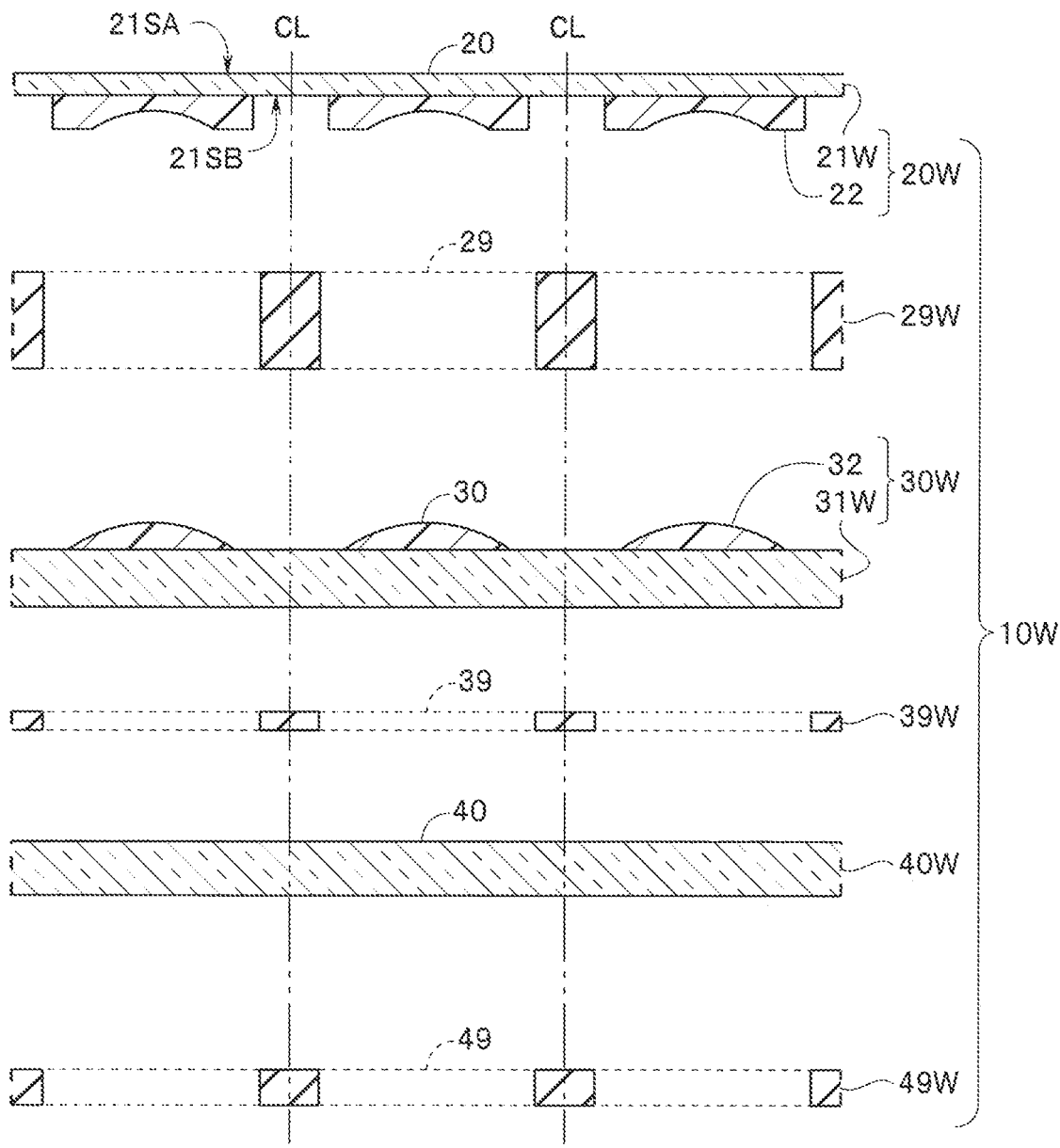
FIG. 5 is a cross-sectional diagram for explaining the manufacturing method of the image pickup apparatus for endoscope of the first embodiment.

As illustrated in FIG. 5, for example, the glass wafer 21W is prepared. A thickness of the glass wafer 21W is determined in accordance with specifications of the image pickup apparatus 1, and is preferably, for example, equal to or greater than 50 μm and equal to or less than 1 mm to achieve a small image pickup apparatus. Note that if the glass wafer 21W is cut along cut lines CL, glass plates 21 of the optical devices 20 are obtained.

Then, a plurality of resin lenses 22 are respectively disposed at predetermined positions on the second principal surface 21SB of the glass wafer 21W. For example, molded resin lenses 22 are disposed on the second principal surface 21SB by applying a transparent resin for lens and curing the transparent resin for lens by irradiating the transparent resin with ultraviolet light (UV) in a direction from the first principal surface 21SA in a state where a mold (not illustrated) having a predetermined shape is pressed against the second principal surface 21SB.

Note that the resin lenses 22 and 32 formed with different resins may be disposed on the optical wafers 20W and 30W.

Figure 6:
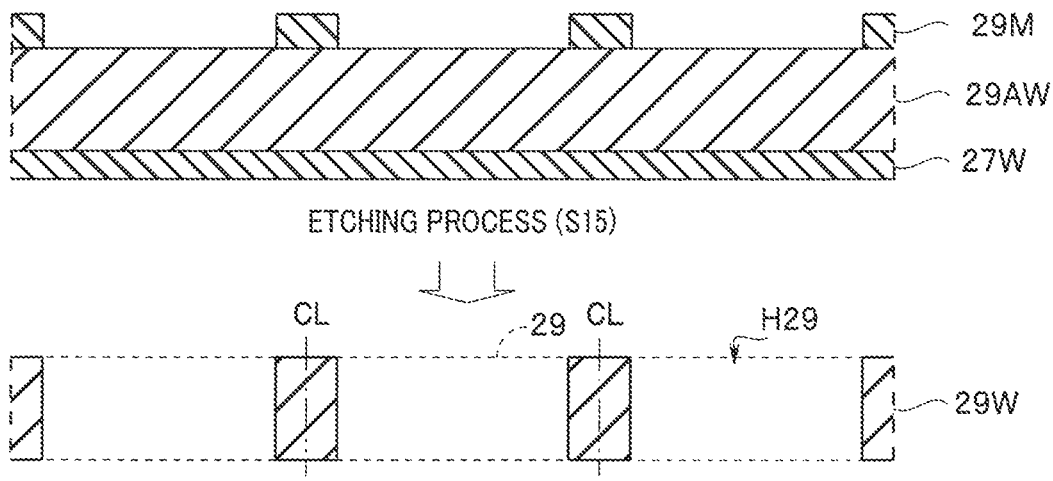
FIG. 6 is a cross-sectional diagram for explaining a manufacturing method of a spacer of the image pickup apparatus for endoscope of the first embodiment.

On the other hand, as illustrated in FIG. 6, in a manufacturing process of the spacer wafer 29W which become a plurality of spacers 29, an etching mask 29M for forming space which becomes an optical path is disposed on a principal surface of a silicon wafer 29AW. A support wafer 27W is bonded to a principal surface (back surface) facing the principal surface on which the etching mask 29M is disposed.

In an etching process (step S15), the spacer wafer 29W including a plurality of through-holes H29 which are space which becomes optical paths is manufactured. For example, dry etching using an ICP-RIE method, or the like, or wet etching using an alkali solution such as potassium hydroxide (KOH) and tetramethylammonium hydroxide (TMAH) is performed. After the etching process S15, the etching mask 29M and the support wafer 27W are removed. The through-holes H29 may be formed through sandblasting or laser machining.

Spacer wafers 39W and 49W which become a plurality of spacers 39 and 49 are manufactured using a method similar to the manufacturing method of the spacer wafer 29W (see FIG. 5).

A material of the spacer wafers 29W, 39W and 49W is not limited to silicon and may be, for example, ceramics such as silicon nitride, glass or a metal such as gold, titanium and aluminum if the material is an inorganic material which has low moisture permeability and which can be directly bonded to the glass wafers.

As described above, in the wafer manufacturing process S10, two optical wafers 20W and 30W which respectively have the glass wafers 21W and 31W as base substrates, and at least one of which is a hybrid lens wafer including a plurality of resin lenses 22 and 32, and the spacer wafers 29W, 39W and 49W which include a plurality of spacers 29, 39 and 49 and which are formed with an inorganic material, are manufactured.

Note that as already described above, for example, the thermal expansion coefficient α29 of the spacer wafer 29W which becomes the spacer 29 is preferably equal to or greater than 50% or equal to or less than 200% of the thermal expansion coefficients α21 and α31 of the glass wafers 21W and 31W which become the glass plates 21 and 31.

Further, a configuration of the optical member 10 can be variously modified in accordance with specifications. In other words, in the wafer manufacturing process of the embodiment, a plurality of optical wafers which respectively have glass wafers as base substrates, and at least one of which is a hybrid lens wafer including a plurality of resin lenses, and at least one spacer wafer, each of which includes a plurality of spacers and which is formed with an inorganic material, are manufactured.

<Step S20> Bonding Process

As illustrated in FIG. 5, the bonded wafer 10W in which space in which a plurality of resin lenses 22 and 32 are respectively disposed is hermetically sealed is manufactured by directly bonding the optical wafers 20W, 30W and 40W to the spacer wafers 29W, 39W and 49W at a temperature lower than a softening point of the resin lenses 22 and 32. For example, the spacer wafer 29W is directly bonded in a state where the spacer wafer 29W is put between the two optical wafers 20W and 30W.

For example, in a case where surface activated bonding is used as direct bonding, for example, first, a surface is activated by performing ion milling treatment in which the bonding surfaces of the optical wafers 20W and 30W and the spacer wafer 29W are irradiated with, for example, argon atom beams for three minutes.

Then, the optical wafers 20W and 30W are stacked in a state where the spacer wafer 29W is put between the optical wafers 20W and 30W in high vacuum in which ultimate vacuum is equal to or less than $10^{-4}$ Pa, and after the optical wafers 20W and 30W and the spacer wafer 29W are bonded by a pressure ($1N/mm^2$) being applied for ten minutes at an ambient temperature, heat treatment is performed for one hour at 120° C.

A bonding temperature is lower than the softening point of the resin lenses 22 and 32, and thus, optical characteristics do not degrade due to change of shapes of the resin lenses 22 and 32.

Note that the bonding surfaces are preferably polished to be smooth at the atomic level through CMP (chemical mechanical polishing), or the like. For example, the respective bonding surfaces are processed so as to have surface roughness in which a maximum height (Rmax) defined in JIS-B0601:2001 is equal to or less than 10 nm or center line average roughness (Ra) is equal to or less than 1 nm.

On the other hand, in a case where anodic bonding is used as direct bonding, for example, the optical wafers 20W and 30W are stacked in a state where the spacer wafer 29W is put between the optical wafers 20W and 30W, and a negative voltage of approximately 400 V is applied to the optical wafers 20W and 30W in a state where the optical wafers 20W and 30W are bonded by a pressure ($1N/mm^2$) being applied and heated to 150° C., and the spacer wafer 29W is set at a ground potential.

In a case of anodic bonding, lithium doped glass is preferably used as the glass wafers 21W and 31W of the optical wafers 20W and 30W. The lithium doped glass can be anodically bonded to silicon in a heated state at lower than, for example, 250° C. which is lower than the softening point of the glass resin lenses 22 and 32.

Direct bonding conditions are selected as appropriate in accordance with the material of the optical wafers 20W and 30W and the material of the spacer wafer 29W. For example, plasma irradiation treatment may be used in activation in surface activated bonding. Further, compression bonding conditions are selected from conditions of, for example, a pressure: from 0.1 $N/mm^2$ to 10 $N/mm^2$, a time period: from one minute to one hour, a temperature: from an ambient temperature to 200° C.

The optical wafer 40W and the spacer wafers 39W and 49W are also directly bonded using a method similar to the bonding method of the optical wafer 30W, or the like. All the wafers may be bonded at the same time or the wafers may be sequentially bonded. Further, a plurality of wafers of the bonded wafer 10W may be directly bonded using different methods. For example, the optical wafers 20W and 30W and the spacer wafer 29W are bonded using surface activated bonding, and the optical wafers 30W and 40W and the spacer wafers 39W and 49W may be anodically bonded. Still further, a resin lens may be disposed on the glass wafer to which the spacer wafer is bonded in advance.

Note that the spacer wafers 39W and 49W in which a resin lens is not disposed and which constitute an optical path may be bonded using an adhesive. However, the spacer wafers 39W and 49W are preferably directly bonded in a similar manner to the optical wafer 30W to prevent moisture from entering the optical path.

<Step S30> Image Pickup Member Disposing Process

Figure 7:
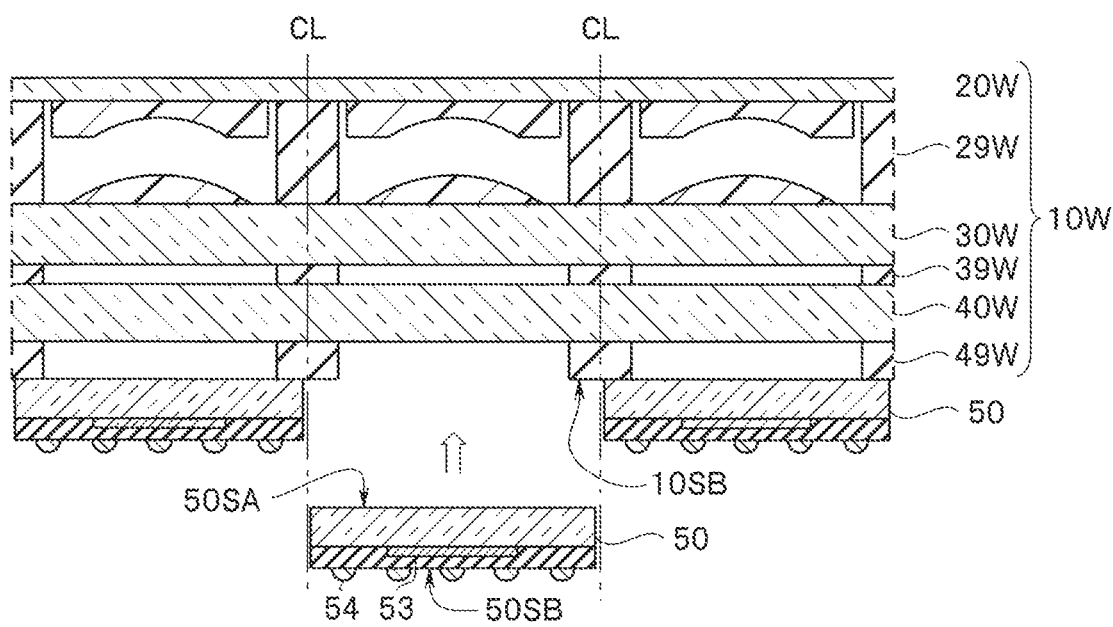
FIG. 7 is a cross-sectional diagram for explaining the manufacturing method of the image pickup apparatus for endoscope of the first embodiment.

As illustrated in FIG. 7, front surfaces 50SA of a plurality of image pickup members 50 are bonded to the rear surface 10SB of the bonded wafer 10W.

In the manufacturing method of the image pickup member 50, first, a light receiving member 53 such as a CMOS light receiving element is formed at a semiconductor wafer using a publicly known semiconductor manufacturing method. Then, an image pickup device wafer (not illustrated) in which the light receiving member 53 is connected to the external electrode 54 of the back surface 50SB is manufactured by manufacturing a through wiring (not illustrated).

The image pickup member 50 including the image pickup device 51 and the cover glass 52 is manufactured by the cover glass wafer being bonded to the image pickup device wafer using an adhesive layer (not illustrated) and cut. The cover glass wafer may be bonded to the image pickup device wafer before the through wiring is manufactured.

<Step S40> Separation Process

The image pickup apparatus 1 including the optical member 10 and the image pickup member 50 illustrated in FIG. 3 is manufactured by cutting the bonded wafer 10W in which a plurality of image pickup members 50 are bonded. The four side surfaces 10SS of the optical member 10 which is separated into pieces using a dicing saw, or the like, have notches which are minute irregularities. In other words, the four side surfaces 10SS of the optical member 10 which is a wafer level structure are cut surfaces. The plurality of optical devices and spacers constituting the optical member 10 have the same external shape and the same external size of cross-sections orthogonal to the optical axis O. All of the plurality of optical devices 20, or the like, have a rectangular parallelepiped shape and have the same shape and the same size of cross-sections in the optical axis orthogonal direction, and thus, the optical member 10 is a quadrangular prism.

The separation process may be, for example, a process of cutting through laser dicing or a process of forming a cut groove through sandblasting or etching.

Note that while, in the image pickup apparatus 1, the cross-section in the optical axis orthogonal direction of the image pickup member 50 has substantially the same shape and substantially the same size as a shape and a size of the cross-section in the optical axis orthogonal direction of the optical member 10, at least one of the shape and the size may be different.

The cross-section in the optical axis orthogonal direction of the image pickup member 50 preferably has a size equal to or less than a size of the cross-section in the optical axis orthogonal direction of the optical member 10, and the image pickup member 50 is preferably stored within space which is an extension of the entrance surface 10SA of the optical member 10 in the optical axis direction to make the diameter of the image pickup apparatus 1 smaller.

Further, the image pickup apparatus 1 may be manufactured by directly bonding or joining the image pickup wafer including a plurality of image pickup members to the bonded wafer 10W and cutting the bonded wafer 10W. In other words, the image pickup wafer including a plurality of image pickup members may be disposed on the bonded wafer 10in the image pickup member disposing process S30, and the image pickup wafer including the plurality of image pickup members and the bonded wafer 10 may be cut in the separation process S40. In this case, the cross-section in the optical axis orthogonal direction of the image pickup member 50 has the same shape and the same size as a shape and a size of the cross-section in the optical axis orthogonal direction of the optical member 10.

The above-described manufacturing method enables a large number of image pickup apparatuses 1 which have a small diameter and which excel in resistance to moisture to be easily manufactured. The image pickup apparatus 1 is disposed at the rigid distal end portion 90A of the endoscope 9.

Note that the cover glass 52 corresponds to an optical device having a glass plate as a base substrate. In other words, the cover glass wafer is also an optical wafer.

In other words, the bonded wafer in which space in which a plurality of resin lenses are disposed is hermetically sealed is manufactured by directly bonding the spacer wafer, the cover glass wafer and the hybrid lens wafer including a plurality of resin lenses in a state where the spacer wafer is put between the cover glass wafer and the hybrid lens wafer at a temperature lower than a softening point of the resin lenses.

The bonded wafer including the cover glass wafer may be separated into pieces after a plurality of image pickup devices 51 which do not include a cover glass are bonded to the bonded wafer. Further, the bonded wafer may be manufactured by bonding a cover glass wafer in which a plurality of image pickup devices 51 are provided in advance to the hybrid lens wafer, and the bonded wafer may be separated into pieces.

Note that the side surfaces of the image pickup apparatus 1 are preferably covered with a light shielding material to prevent external light from entering the optical path. In a case where the light shielding material also serves as a moisture resistant material, the image pickup apparatus 1 excels in resistance to moisture, so that it is possible to make the light shielding material (moisture resistant material) thinner and achieve a smaller diameter.

Figure 8:
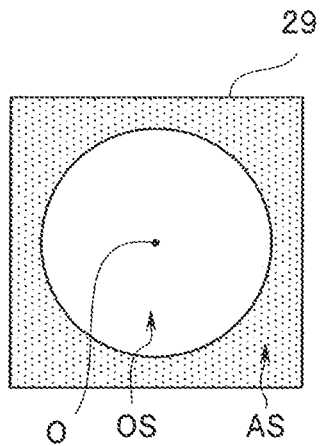
FIG. 8 is a cross-sectional diagram of the spacer of the image pickup apparatus for endoscope of the first embodiment.

As illustrated in FIG. 8, while a cross-section orthogonal to the optical axis O of the spacer 29, or the like, has a rectangular external shape, an inner shape of a through-hole which is an optical path region OS has a cylindrical shape. Further, the whole of upper and lower surfaces of the spacer 29 are bonded surfaces AS, and the spacer 29 is bonded to the optical devices 20 and 30 without other members such as an adhesive being put between the spacer 29 and the optical devices 20 and 30. Note that the optical path region OS defined by the spacer 29 is not limited to the cylindrical shape and may be, for example, a prismatic shape, an oval cylindrical shape or other shapes.

In a case where the spacer is bonded to the two optical devices using an adhesive, there is a possibility that the adhesive may enter the optical path region OS, and thus it is necessary to make an external size larger to secure a wide adhesive area.

In the image pickup apparatus 1, the whole of the upper and lower surfaces of the spacer become the bonded surfaces, and thus, high bonding strength can be achieved, and an adhesive does not enter the optical path region OS on an inner periphery side. An interval between the optical path region OS and the bonded surface AS can be designed to be small in the image pickup apparatus 1, and thus, the image pickup apparatus having a small external size and a small diameter can be achieved. For example, the interval between the optical path region OS and the bonded surface AS can be set at several μm to 100 μm which is positioning tolerance. The endoscope 9 including the image pickup apparatus 1 has a small-diameter rigid distal end portion 90A, and thus, is less invasive.

Figure 9:
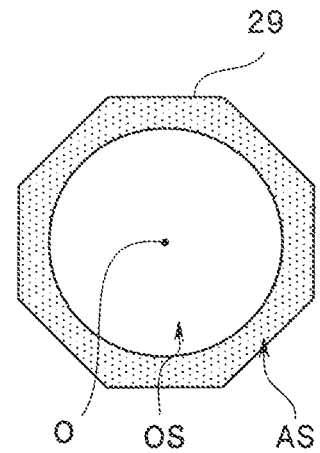
FIG. 9 is a cross-sectional diagram of the spacer of the image pickup apparatus for endoscope of the first embodiment.

Note that as illustrated in FIG. 9, the cross-section orthogonal to the optical axis O of the spacer 29 may have a polygonal (octagonal) external shape in which corner portions are chamfered or a circular external shape. In other words, the image pickup apparatus 1 may have a polygonal prism external shape or a cylindrical external shape having a smaller cross-section orthogonal to the optical axis O than a cross-section of a quadrangular prism.

Second Embodiment

Image pickup apparatuses for endoscope 1A to 1C and endoscopes 9A to 9C including the image pickup apparatuses 1A to 1C of a second embodiment to a fourth embodiment described below are similar to the image pickup apparatus 1 and the endoscope 9 and have the same functions, and thus, the same reference numerals will be assigned to components having the same functions, and description will be omitted.

Figure 10:
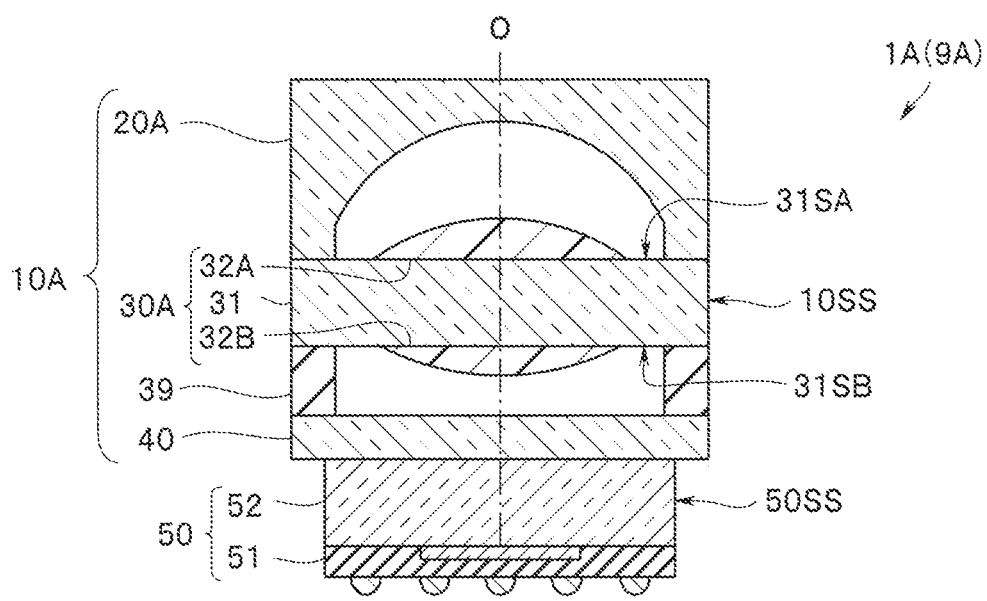
FIG. 10 is a cross-sectional diagram of an image pickup apparatus for endoscope of a second embodiment.

In the image pickup apparatus for endoscope 1A of the second embodiment illustrated in FIG. 10, the optical member 10A includes three optical devices 20A, 30A and 40, and one spacer 39. The optical device 20A is a glass member having functions of a concave lens and a spacer. In the optical device 30A which has the glass plate 31 as a base substrate, the resin lens 32A is disposed on the third principal surface 31SA, and the resin lens 32B is disposed on the fourth principal surface 31SB. The optical device 40 is an infrared cut filter device having a function of blocking infrared light.

Further, the image pickup member 50 has a smaller external size of a cross-section orthogonal to the optical axis O than an external size of a cross-section of the optical member 10A. Thus, the side surfaces 10SS of the optical member 10A are not positioned on the same planes as planes of the side surfaces 50SS of the image pickup member 50.

The image pickup apparatus 1A has the same effects as the effects of the image pickup apparatus 1 of the first embodiment, and the spacer 29 can be omitted, so that it is possible to simplify a structure and easily manufacture the image pickup apparatus 1A.

Third Embodiment

Figure 11:
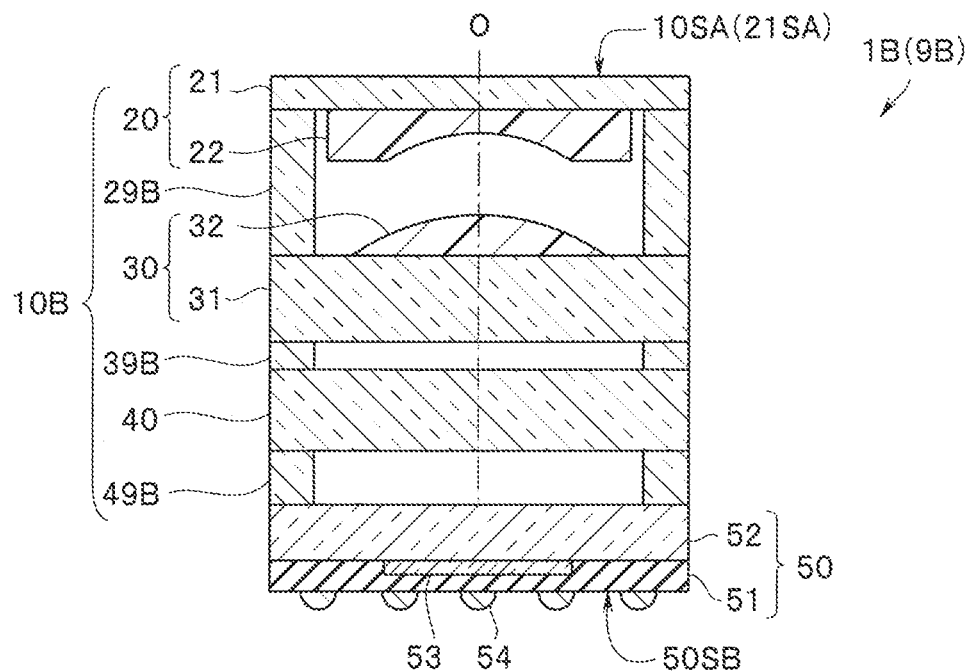
FIG. 11 is a cross-sectional diagram of an image pickup apparatus for endoscope of a third embodiment.

In the image pickup apparatus for endoscope 1B of the present embodiment illustrated in FIG. 11, the spacers 29B, 39B and 49B are constituted with the same type (same composition) of glass as a type of glass of the glass plates 21, 31 and 40.

Thus, the glass plates 21, 31 and 40 can be easily directly bonded to the spacers 29B, 39B and 49B. Further, the glass plates 21, 31 and 40 and the spacers 29B, 39B and 49B have the same thermal expansion coefficient α, and thus, reliability of the image pickup apparatus 1B and the endoscope 9B does not degrade by temperature change upon manufacturing and when used.

Note that in the third embodiment, it is only necessary that at least the spacer 29B in which space in which the resin lenses 22 and 32 are disposed is hermetically sealed be constituted with the same type of glass as a type of the glass of the glass plates 21 and 31. For example, the spacers 39B and 49B may be constituted with silicon.

Note that spacers except the spacer 29B may be various kinds of inorganic materials, for example, ceramics such as silicon nitride or a metal such as gold, titanium and aluminum if the spacers can be easily directly bonded to glass plates of optical devices and have thermal expansion coefficients α equal to or greater than 50% and equal to or less than 200% of thermal expansion coefficients α of the glass plates.

Fourth Embodiment

Figure 12:
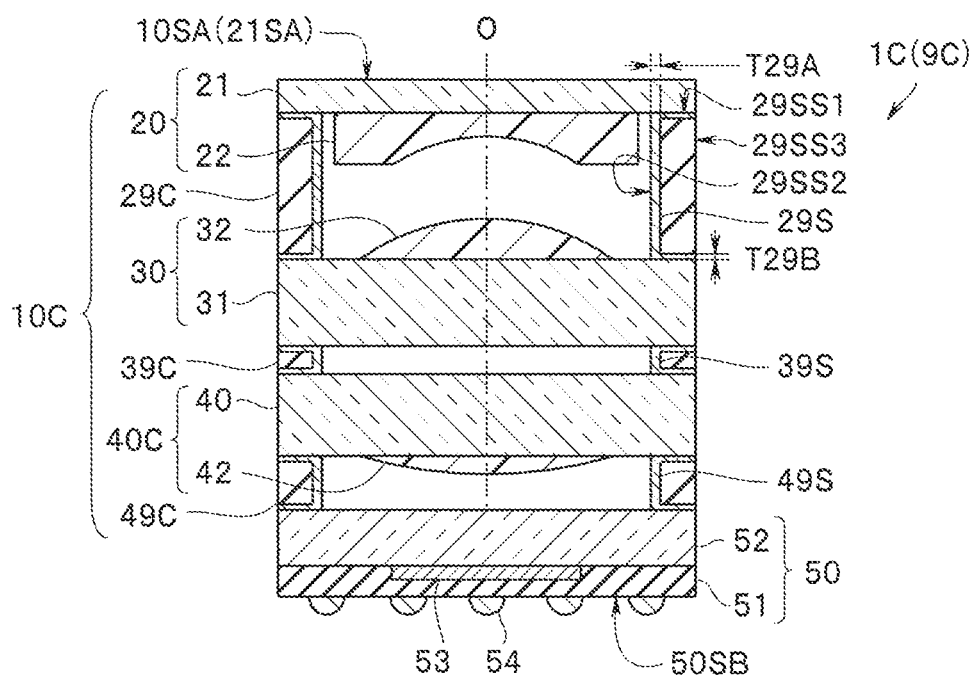
FIG. 12 is a cross-sectional diagram of an image pickup apparatus for endoscope of a fourth embodiment.

In the image pickup apparatus for endoscope 1C of the present embodiment illustrated in FIG. 12, for example, silicon oxide layers 29S, 39S and 49S are formed on the bonded surfaces of the spacers 29C, 39C and 49C having silicon as a base material.

Figure 13:
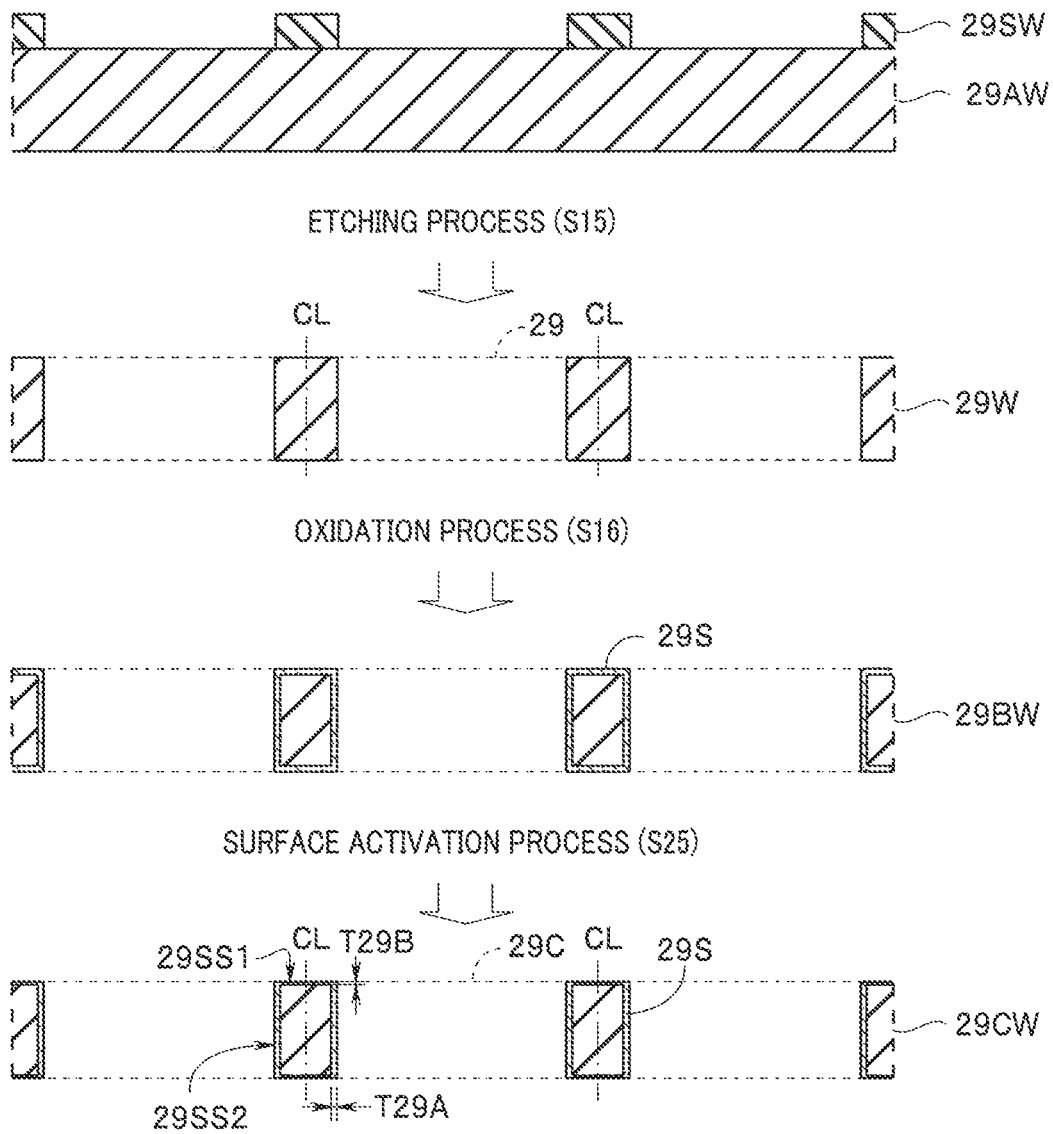
FIG. 13 is a cross-sectional diagram for explaining a manufacturing method of a spacer of the image pickup apparatus for endoscope of the fourth embodiment.

For example, as illustrated in FIG. 13, a manufacturing method of the spacer 29C includes an oxidation process (step S16) in which a surface of the spacer wafer 29W is oxidized to make the spacer wafer 29BW after the etching process S15 in the wafer manufacturing process S10.

The oxidation process S16 is oxygen plasma treatment or heating treatment under an oxidizing atmosphere.

Then, in a surface activation process (step S25) of the bonding process, a surface of the bonded surface 29SS1 of the spacer wafer 29BW on which the silicon oxide layer 29S is formed is slightly removed. Thus, a thickness T29B of the silicon oxide layer 29S of the bonded surface 29SS1 of the spacer wafer 29CW is thinner than a thickness T29A of the silicon oxide layer 29S of an inner surface 29SS2.

In other words, the spacer in which a thickness of an oxide layer on the bonded surface is thinner than a thickness of an oxide layer on the inner surface can be regarded as being bonded through surface activated bonding. Further, the optical member 10C in which the oxide layer is not formed on the side surfaces of the spacer can be regarded as a wafer level optical member manufactured by separating the bonded wafer into pieces.

In the image pickup apparatus for endoscope 1C, for example, the glass plates 21 and 31 which are oxides, can be easily bonded to the oxide layer of the spacer 29C or the like through direct bonding, particularly, surface activated bonding, and high bonding reliability can be achieved. Note that the oxide layer of the spacer 29C or the like is a layer in which silicon of the spacer 29C is oxidized and is not regarded as other members of the spacer 29C. In other words, the glass plates 21 and 31 are bonded to the spacer 29C without other members being put between the glass plates 21 and 31 and the spacer 29C.

In the image pickup apparatus for endoscope 1C, a resin lens 42 is disposed on an infrared cut filter substrate 40 formed with glass in the optical device 40C. Further, the cover glass 52 of the image pickup member 50 is directly bonded to the spacer 49S.

In other words, the resin lens 42 is hermetically sealed in space surrounded by the infrared cut filter substrate 40, the cover glass 52 and the spacer 49S.

Note that the spacer wafer 29C, or the like, is not limited to silicon and may be, for example, aluminum or titanium if the spacer wafer 29C, or the like, is an inorganic material which allows an oxide layer to be formed on a surface in the oxidation process S16.

It goes without saying that the endoscopes 9A to 9C including the image pickup apparatuses 1A to 1C have effects of the image pickup apparatuses 1A to 1C in addition to the effects of the endoscope 9.

The present invention is not limited to the above-described embodiments, or the like, and various changes, combinations and application are possible within a range not deviating from the gist of the invention.

What is claimed is:
1. A method of manufacturing a plurality of image pickup apparatuses, each for use with an endoscope, the method comprising:
   manufacturing two optical wafers each comprising a glass wafer, at least one of the two optical wafers being a hybrid lens wafer including a plurality of resin lenses formed on the glass wafer, and
   providing a spacer wafer including a plurality of spacers formed with an inorganic material between the two optical wafers;
   directly bonding the spacer wafer to the two optical wafers to form a plurality of hermetically sealed spaces in which the plurality of resin lenses is respectively disposed, the bonding being at a temperature lower than a softening point of the plurality of resin lenses;
   disposing a plurality of image pickup members, each having an image sensor, on the bonded wafer respectively corresponding to the plurality of lenses; and cutting the two bonded optical wafers with the plurality of image pickup members disposed thereon to form a plurality of the image pickup apparatuses such that each of the plurality of image pickup apparatuses comprise:
an optical member comprising two glass plates respectively formed from the two glass wafers, at least one of which having a resin lens of the plurality of resin lenses; plate and
a spacer of the plurality of spacers disposed between the two glass plates, and an image pickup member of the plurality of image pickup members.

2. The method according to claim 1, wherein a thermal expansion coefficient of the spacer wafer is equal to or greater than 50% and equal to or less than 200% of a thermal expansion coefficient of the glass wafer.

3. The method according to claim 1, wherein the spacer wafer comprises a same type of glass as a type of glass of the glass wafer.

4. The method according to claim 1, wherein the spacer wafer is manufactured by etching a silicon wafer.

5. The method according to claim 4, wherein the spacer wafer is manufactured by oxidizing a surface of the spacer wafer after the etching.

\* \* \* \* \*